ns Patent

United States Patent [19]

Wang

[11] Patent Number: 4,530,933
[45] Date of Patent: Jul. 23, 1985

[54] 8-AZA-13-THIAPROSTANOIDS AND A METHOD OF USE THEREOF AS ANTI-ULCER AGENTS

[75] Inventor: Chia-Lin J. Wang, Wilmington, Del.

[73] Assignee: E. I. Du Pont de Nemours and Company, Wilmington, Del.

[21] Appl. No.: 452,882

[22] Filed: Dec. 27, 1982

[51] Int. Cl.³ .................... C07D 207/26; A61K 31/40
[52] U.S. Cl. .................... 514/425; 514/926; 514/925; 548/543; 548/547
[58] Field of Search ................ 548/547, 543; 424/274

[56] References Cited

U.S. PATENT DOCUMENTS

| | | | |
|---|---|---|---|
| 3,975,399 | 9/1976 | DeFranco et al. | 424/244 X |
| 4,003,911 | 1/1977 | Scribner | 424/274 X |
| 4,032,533 | 6/1977 | Scribner | 424/270 X |
| 4,113,873 | 9/1978 | Himizu et al. | 424/274 X |
| 4,115,401 | 9/1978 | Nanthavong et al. | 424/274 X |
| 4,117,346 | 12/1979 | Nelson | 542/427 |
| 4,209,639 | 6/1980 | Wissner | 562/426 |
| 4,211,876 | 7/1980 | Scribner | 548/367 |
| 4,320,136 | 3/1982 | Scribner | 424/274 |

OTHER PUBLICATIONS

Novak et al., Tetrahedron Letters, vol. 38, No. 1, pp. 153–159, 1982.

Primary Examiner—Richard L. Raymond
Assistant Examiner—D. B. Springer
Attorney, Agent, or Firm—James A. Costello

[57] ABSTRACT

Biologically active 8-aza-13-thiaprostanoids having the formula:

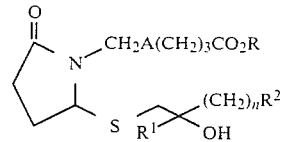

wherein
A is CH=CH (cis or trans), C≡C, $CH_2CH_2$,

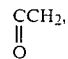

or $CHOHCH_2$;

R is H, $C_1$ to $C_{12}$ n-alkyl, branched chain alkyl, or cycloalkyl, or a physiologically acceptable metal or amine salt cation;
$R^1$ is H, $CH_3$ or $C_2H_5$;
$R^2$ is $CH_3$ or $CF_3$; and
n is an integer from 4 to 9.

16 Claims, No Drawings

8-AZA-13-THIAPROSTANOIDS AND A METHOD OF USE THEREOF AS ANTI-ULCER AGENTS

BACKGROUND OF THE INVENTION

This invention concerns biologically active 8-aza-13-thiaprostanoids.

There are many references in the literature to prostanoids, a term which is generic to natural and synthetic prostaglandins and prostaglandin-like compounds. It is well known in connection with these prostanoids that even slight differences in chemical structures or stereochemical configurations will have profound effects on biological activity.

Prostanoids have a five-membered ring bearing relatively lengthy substituents on adjacent ring atoms. In most of the known prostanoids, the rings are carbocyclic; in a few of these compounds one of the side chains bears a sulfur atom in the $C_{13}$ position. Representative of the prostanoids that contain a carbocyclic ring and a sulfur atom in a side chain are those described in the following publications.

U.S. Pat. No. 4,209,639 discloses prostaglandins having the formula:

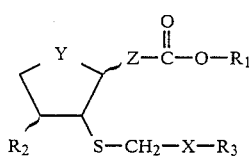

wherein Y is a divalent radical selected from the group consisting of

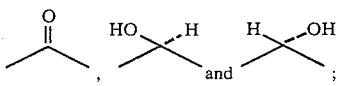

$R_2$ is selected from the group consisting of H, OH, and lower alkanoyloxy; $R_1$ is hydrogen or an alkyl of 1 to 12 carbons; $R_3$ is hydrogen, an alkyl of 4 to 7 carbons or a phenoxymethyl group in which the phenyl ring is optionally substituted; X is a divalent radical comprising carbon, hydrogen, and OH; and Z is a divalent radical selected from a number of substituent groups, none of which contains nitrogen.

U.S. Pat. No. 4,309,441 discloses prostaglandins having the formula:

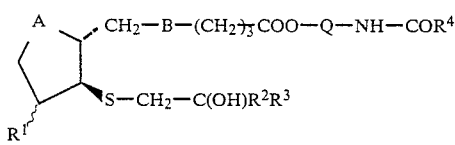

wherein A is —CO— or —CHOH—; B is —$CH_2CH_2$— or —CH=CH—; Q is 1,4-phenylene or 1,4-naphthylene; $R^1$ is H or OH; $R^2$ is H or $CH_3$; $R^3$ is alkyl with 1 to 8 carbon atoms or alkyl with 1 to 8 carbon atoms substituted by (a) phenyl, (b) phenyl substituted by at least one of $CH_3$, F, Cl, Br, OH, $OCH_3$ or $CF_3$, (c) phenoxy or (d) phenoxy substituted by at least one of $CH_3$, F, Cl, Br, OH, $OCH_3$ or $CF_3$; and $R^4$ is $NH_2$, $CH_3$, phenyl, p-acetylaminophenyl, p-benzoylaminophenyl or pentylamino. These prostaglandins contain no aza nitrogen.

Novak et al., in Tetrahedron, Vol. 38, No. 1, pages 153 to 159 (1982) also disclose prostaglandins that contain no nitrogen:

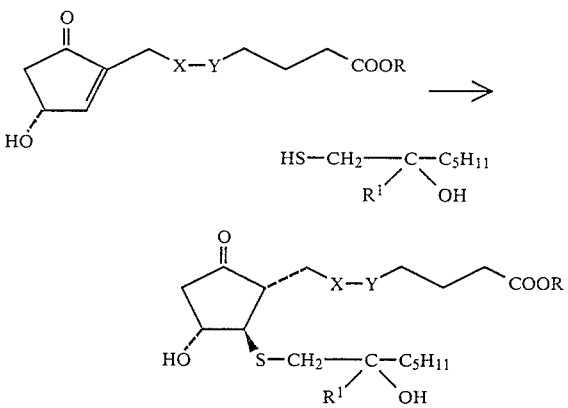

wherein X and Y are $CH_2$—$CH_2$ or

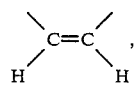

and R and R' are H or $CH_3$.

Two recent publications that discuss the phenomenon of cytoprotection by prostaglandins are Robert et al., Gastroent., 77, 433 to 443 (1979) and Robert, Scand. J. Gastroent., 16, Suppl. 67, 223 to 227 (1981). These publications describe several of the uses including antiulcer use, to which the compounds of this invention may be put. In this regard, see especially pages 442 to 443, and 226 to 227, respectively.

The prostanoids now described differ from those disclosed in these publications primarily in that they combine the following structural features (designated by conventional prostanoid numbering): a single nitrogen atom at position 8 in a heterocyclic five-membered ring and a carbonyl group in the five-membered ring at position 9 (making them lactams).

Other representative heterocycle-based prostanoids that do not, however, contain sulfur are the aza- and diaza-prostanoids disclosed in U.S. Pat. No. 3,873,566 (Scribner), U.S. Pat. No. 3,975,399 (DeFranco and Scribner), U.S. Pat. No. 4,003,911 and U.S. Pat. No. 4,032,533 (Scribner), U.S. Pat. No. 4,113,873 (Himizu), U.S. Pat. No. 4,177,346 (Nelson), U.S. Pat. No. 4,211,876 (Scribner), and Belgium Pat. No. 854,268 (Hoechst).

SUMMARY OF THE INVENTION

The compounds of this invention have the formula:

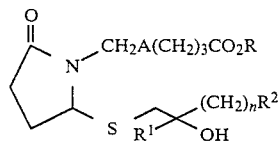

wherein
A is CH=CH (cis or trans), C≡C, $CH_2CH_2$,

or CHOHCH$_2$;

R is H, C$_1$ to C$_{12}$ n-alkyl, branched chain alkyl, or cycloalkyl or a physiologically acceptable metal or amine salt cation;

R$^1$ is H, CH$_3$ or C$_2$H$_5$;

R$^2$ is CH$_3$ or CF$_3$; and n is an integer from 4 to 9.

Preferred compounds are those wherein the stereochemical configuration is as follows:

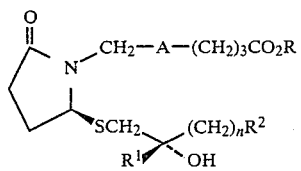

and wherein A is C$_2$H$_4$, C(O)CH$_2$ or CHOHCH$_2$; R is H, CH$_3$ or C$_2$H$_5$; R$^1$=R$^2$=CH$_3$; and n is 4 to 6. The most preferred compounds are those wherein: (i) A is C$_2$H$_4$, R is C$_2$H$_5$, and n is 4; and (ii) A is C$_2$H$_4$, R is H, and n is 4. These compounds exhibit cytoprotective activity.

DETAILS OF THE INVENTION

Typical reaction procedures are provided in the Examples. It will be obvious to one skilled in the art that analogous procedures can be employed to make all the compounds of the invention merely by using appropriate reactants. For example, different alkyl groups, R, can be introduced by reaction of 8 (see Example 2) with the corrresponding alcohol (ROH) in the presence of dicyclohexylcarbodiimide (DCC) and dimethylaminopyridine (DMAP). In Example 1, replacement of ethyl-7-bromoheptanoate with ethyl-7-bromo-5-heptynoate or ethyl-7-bromo-5-heptenoate (cis or trans) will yield a product that can be converted to 9 or 10 by the procedure therein described:

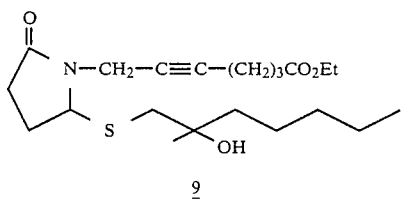

9

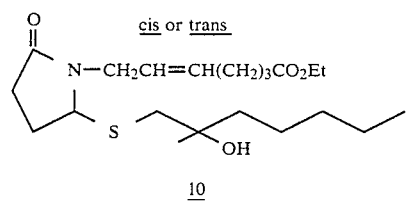

10

In Example 1, if 2-methyl-1-heptene 4 is replaced with 1-heptene or 2-ethyl-1-heptene, the product will be 11 or 12, respectively:

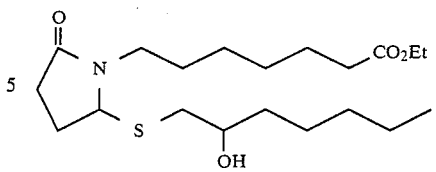

11

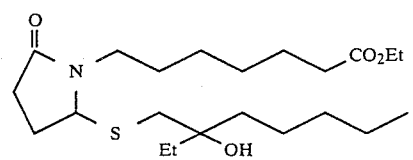

12

The para-toluenesulfonic acid employed in Example 1 can be replaced by other acids or by Lewis acids such as aluminum chloride. Hydrogen chloride gas can be used, and other similar modifications and expedients can be practiced. For instance, a modification that can be employed to make the 1-mercapto-2-methylheptan-2-ol, 6, of Example 1, Step D, is as follows. To a solution of thiourea (3.42 g, 45 mmol) and 1.5 mL of concentrated sulfuric acid in tetrahydrofuran (38 mL) at 0° is added a solution of 2-methyl-1-heptene oxide (4.8 g, 37.5 mmol) in tetrahydrofuran (20 mL) dropwise. The mixture is stirred at 0° for 30 minutes and then room temperature for 0.75 hour. After removing the solvent, a solution of 6.5 g of sodium hydroxide in 26 mL of water is added. After stirring one hour, the solution is washed with ether. The aqueous solution is then poured into a cold solution of 13 mL of concentrated sulfuric acid in 40 mL of water. The mixture is extracted with ether; the ether layer is washed with saturated sodium bicarbonate, saturated aqueous sodium chloride, and then dried over magnesium sulfate. The crude product can be purified by HPLC.

UTILITY

Although a variety of animal models of antiulcer activity exist, most of the procedures were designed to detect compounds that inhibit gastric acid secretion. Tests of this type are not well suited for the study of a class of compounds that have some other mechanism of action. The naturally-occurring prostaglandins represent such a class. A recent focus of research has been to identify prostaglandin analogs that have antiulcer activity but do not have acid secretion influences.

The antiulcer model selected for screening of the azaprostanoids was the cytoprotection model. The cytoprotection model consists of: (a) administration of test compound to rats, (b) oral administration of absolute ethanol 1 hr later, and (c) sacrificing and evaluating the stomach for tissue damage (necrosis) 1 hr after ethanol administration. The rationale of the cytoprotection model is that any compound that accelerates the stomach's own defense mechanisms, e.g., mucous production, will protect the tissues from damage caused by subsequent administration of a necrotizing agent such as strong acid or base, hypertonic salts, or ethanol.

METHOD

The subjects were male Sprague-Dawley rats (GIBCO) that were housed in the animal colony at least five days with ad lib food and water prior to fasting. The rats were deprived of all food 48 hrs prior to testing. The rats weighed 175 to 210 g when a test began.

Test compounds were prepared for injection 1 hr before a test by sonication for 20 sec in 0.05% sodium alginate solution. A stock solution of sodium alginate in water was prepared at least 24 hrs before use. Compounds were injected orally with a 16 gauge intubation probe (Tieman); the injected volume was 0.5 ml per 200 g of body weight and the concentration of compound was 2 mg/kg of body weight. The number of rats per group was 6 to 8. Control rats received vehicle. For drugs applied in ethanolic solution or as formulations of finely divided silica gel (Syloid ®, Davison Company), the vehicle contained a comparable amount of ethanol or silica gel.

One hr after administration of test compound each rat received an oral injection of absolute ethanol with a volume of 1.0 ml per 200 g of body weight. One hr after ethanol administration the rats were sacrificed with $N_2$ gas, the stomachs were removed and cut along the greater curvature. The stomachs were washed in tap water to remove mucous and were refrigerated until they were scored, usually within 1 hr.

Scoring was done "blind" by one of two experienced raters. Each stomach was compared to a series of six standard photographs that depicted no necrosis (a score of zero) through complete necrosis covering the entire (except antral) glandular portion of the stomach (a score of 5). A score was assigned to each stomach on this 0 to 5 scale with a minimum increment of 0.25. For example, a stomach judged to be greater than 1.0 but less than 1.5 in severity of tissue damage received a score of 1.25. After all stomachs were scored the percent protection caused by the test compound was calculated:

$$\text{Percent protection} = 100 - \left( \frac{\text{mean score of test group}}{\text{mean score of control group}} \times 100 \right).$$

For example, if a test group had a mean score of 1.25 and the control group had a mean score of 2.5, the percent protection was:

$$100 - \left( \frac{1.25}{2.5} \times 100 \right) = 50\%.$$

RESULTS

By the method described above, it was found that the preferred compounds of this invention, i.e., those where A is $C_2H_4$, n is 4, $R^1$ and $R^2$ are each $CH_3$, and R is either (i) $C_2H_5$ or (ii) H, showed 44 and 53 percent protection, respectively. Based on these results, it is concluded that all of the compounds of this invention would display useful cytoprotection activity.

The attractiveness of these compounds for drug use is enhanced because they are effective when taken orally as well as by injection. Furthermore, unlike natural prostaglandins of the PGE type, the compounds are quite stable chemically; for example, they would have a long shelf-life and are stable in moderately strong acid or basic media. Finally, the compounds of this invention are inexpensive and easy to make relative to the natural prostaglandins and many of their derivatives.

As pharmaceutical compositions useful for treating animal or human subjects, the compounds of this invention can be formulated as tablets or in capsules for oral administration or in oils for administration by injection. A pharmaceutically acceptable carrier will also usually be employed therewith.

The following Examples illustrate the invention. Proton nuclear magnetic resonance (PMR) chemical shifts are reported in parts per million ($\delta$ units) relative to internal tetramethylsilane standard, i.e., a downfield shift is positive in sign. Coupling constants, J, are reported in Hertz (Hz).

EXAMPLE 1

Step A 7-(2-Oxo-5-oxopyrrolidin-1-yl)heptanoic Acid, Ethyl Ester (2)

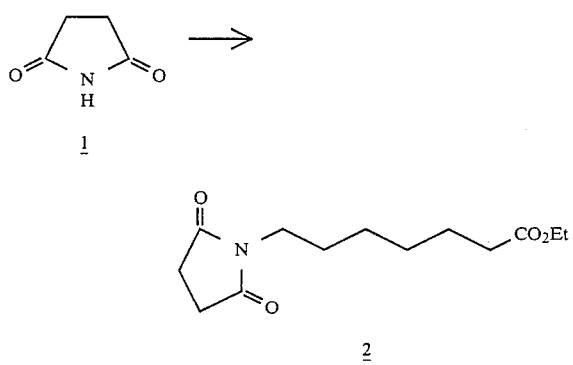

A. A mixture of succinimide (1, 3.2 g, 31.6 mmol) and ethyl 7-bromoheptanoate (5 g, 21 mmol) in dimethylformamide (30 mL) containing potassium carbonate (3.5 g, 25 mmol) was heated at about 55° to 60° C. for twenty hours. The mixture was then diluted with ether and washed twice with water, once with saturated aqueous sodium chloride, and dried over magnesium sulfate. Removal of the solvent under reduced pressure gave the crude product which was purified by high performance liquid chromatography (HPLC) to give 3.66 g of 7-(2-oxo-5-oxopyrrolidin-1-yl)heptanoic acid, ethyl ester, 2. IR (neat): 1775, 1735, 1700 cm$^{-1}$; PMR (CDCl$_3$): $\delta$ 4.10 (q, J=7, 2H), 3.46 (t, J=7, 2H), 2.67 (s, 4H), 2.26 (t, J=7, 2H), 1.77–1.11 (m, 8H), and 1.23 (t, J=7, 3H).

Step B 7-(2-Ethoxy-5-oxopyrrolidin-1-yl)heptanoic Acid, Ethyl Ester (3)

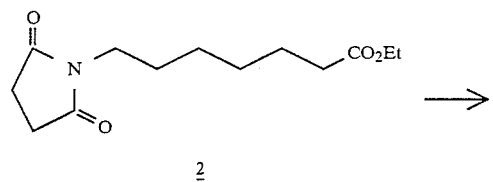

-continued

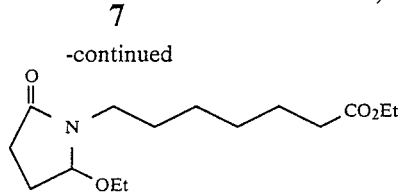

3

To a solution of 2 (1 g, 3.92 mmol) in ethanol (20 mL) at 0° C. was added sodium borohydride (1.04 g, 27.45 mmol). Three drops of 2N hydrochloric acid (in ethanol) were added every fifteen minutes. After stirring for four hours, pH was adjusted to 3 using concentrated hydrochloric acid. The reaction mixture was stirred at 0° C. for 45 min and then poured into saturated sodium bicarbonate solution. This mixture was extracted three times with chloroform. Thin layer chromatography of the crude product showed two spots. The crude product was dissolved in methylene chloride-methanol and treated with triethylorthoformate (1.5 mL) containing para-toluenesulfonic acid (PTSA) at room temperature for 2.5 hours. It was then purified by HPLC to afford 749 mg of 7-(2-ethoxy-5-oxopyrrolidin-1-yl)heptanoic acid, ethyl ester, 3. IR ($CH_2Cl_2$): 1750, 1710 $cm^{-1}$; PMR ($CDCl_3$): δ 4.97 (m, 1H), 4.11 (q, J=7, 2H), 3.44 (q, J=7, 2H), 3.67–1.30 (m, 16H), and 1.22 (2t, J=7, 6H).

Step C

2-Methyl-1-heptene Oxide (5)

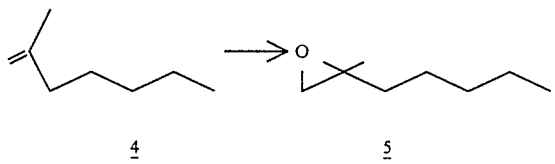

4    5

To a solution of 2-methyl-1-heptene 4 (17 g, 0.15 mol) in methylene chloride (300 mL) at 0° C. was added meta-chloroperbenzoic acid (37 g, 0.18 mol) in portions. The reaction mixture was stirred at 0° C. for 30 minutes, then at room temperature overnight. It was cooled in an ice bath and then filtered. The filtrate was washed with 5% sodium hydroxide, saturated sodium chloride and dried over magnesium sulfate; 7.8 g of 2-methyl-1-heptene oxide 5 was obtained after HPLC purification.

Step D

1-Mercapto-2-methylheptan-2-ol (6)

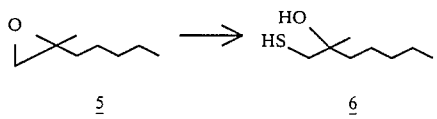

5    6

Hydrogen sulfide gas was bubbled into a solution of 5 (3.84 g, 30 mmol) in tetrahydrofuran (30 mL) containing diisopropylamine (21 mL, 150 mmol) for one hour and the reaction mixture was stirred at room temperature for 68 hours. It was diluted with ether and washed with 10% aqueous hydrogen chloride, saturated sodium bicarbonate solution, and saturated aqueous sodium chloride. The organic layer was dried over magnesium sulfate. The solvent was evaporated in vacuo; 1.2 g of 1-mercapto-2-methylheptan-2-ol 6 was obtained after HPLC purification. IR (neat): 3600–3200 $cm^{-1}$ (br); PMR ($CDCl_3$): δ 2.67 (s, 1H), 2.57 (s, 1H), 2.17 (s, 1H), 1.70–1.20 (m, 9H), 1.22 (s, 3H), and 0.90 (t, 3H).

Step E

7-[2-(2-Hydroxy-2-methylheptylthio)-5-oxo-pyrrolidin-1-yl]heptanoic Acid, Ethyl Ester (7)

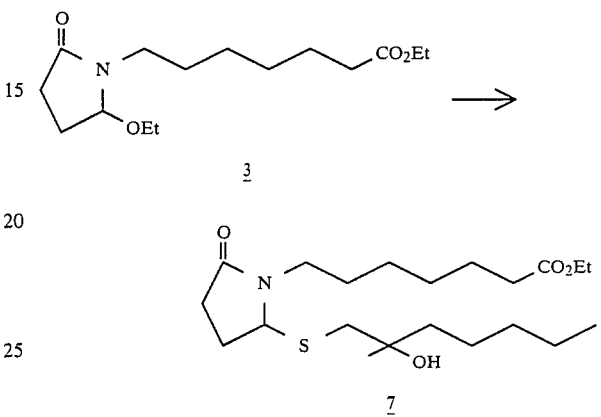

A mixture of 3 (30 mg, 0.1 mmol) and 6 (16.2 mg, 0.1 mmol) in methylene chloride (3 mL) containing para-toluenesulfonic acid (10 mg) was stirred at room temperature for one hour. It was then diluted with ether and washed with saturated sodium bicarbonate, saturated sodium chloride solution, and dried over magnesium sulfate. Removal of the solvent gave 57 mg of the crude product. In another run, a mixture of 3 (1.93 g, 6.79 mmol) and 6 (1.1 g, 6.79 mmol) in methylene chloride (20 mL) containing PTSA (200 mg) was stirred at room temperature for 4 hours. Using the foregoing work-up procedure the crude product obtained was combined with the previous one. HPLC purification gave 2.48 g of pure 7-[2-(2-hydroxy-2-methylheptylthio)-5-oxo-pyrrolidin-1-yl]heptanoic acid, ethyl ester, 7. IR (neat): 3485, 1750, 1700 $cm^{-1}$; PMR ($CDCl_3$): δ 4.72 (m, 1H), 4.07 (q, J=7, 2H), 3.57 (m, 1H), 3.03 (m, 1H), 2.60–1.00 (m, 31H), and 0.87 (t, 3H); MS: m/z 240.1595 (M+-lower side chain). Calcd. for $C_{13}H_{22}NO_3$: 240.1599.

Example 2

7-[2-(2-Hydroxy-2-methylheptylthio)-5-oxo-pyrrolidin-1-yl]heptanoic Acid (8)

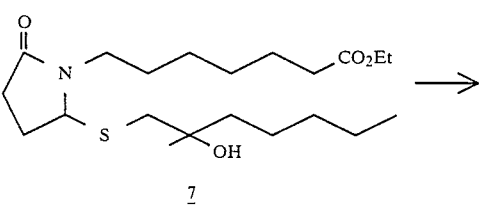

7

-continued

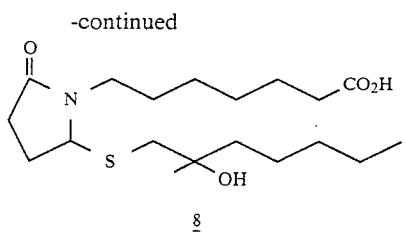

A mixture of 7 (300 mg, 0.75 mmol) in ethanol (3 mL) containing 2 mL of 10% potassium hydroxide was stirred at room temperature for 1.75 hours. After removing ethanol, the aqueous layer was extracted once with ether; after acidification with 10% hydrogen chloride, it was extracted three times with ethyl acetate. The combined ethyl acetate layer was dried over magnesium sulfate. Evaporation of the solvent in vacuo gave 279 mg of 7-[2-(2-hydroxy-2-methylheptylthio)-5-oxopyrrolidin-1-yl]heptanoic acid 8. IR ($CH_2Cl_2$): 3600–2500 (br), 1715, 1695 cm$^{-1}$; PMR ($CDCl_3$): δ 6.23 (bs, 2H, —$CO_2H$ and —OH), 4.72 (m, 1H), 3.60 (m, 1H), 3.07 (m, 1H), 2.70–1.10 (m, 27H) and 0.88 (t, 3H); MS: m/z 212.1288 (M$^+$-lower side chain), Calcd. for $C_{11}H_{18}NO_3$: 212.1287.

EXAMPLE 3

Step A 7-(2-Oxo-5-oxopyrrolidin-1-yl)-1,6-bistetrahydropyranyl heptanyl Ether (13)

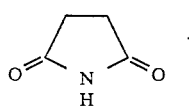

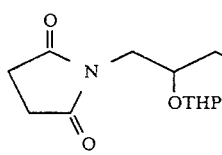

To a mixture of succinimide (1) (297 mg, 3 mmol) and potassium carbonate (414 mg, 3 mmol) in dimethylformamide (3 mL) was added a solution of 7-bromo-1,6-bistetrahydropyranyl heptanyl ether (379 mg, 1 mmol) in dimethylformamide (2 mL). The reaction mixture was heated at about 80° overnight. It was then diluted with ether, washed twice with water, once with saturated sodium chloride, and dried over magnesium sulfate. The crude product was purified by flash column chromatography to give 264 mg of pure 7-(2-oxo-5-oxo-pyrrolidin-1-yl)-1,6-bistetrahydropyranyl heptanyl ether (13). IR ($CH_2Cl_2$): 1705 cm$^{-1}$; PMR ($CDCl_3$): δ 4.80–3.15 (m, 11H), 2.68 (2s, 4H), and 2.00–1.50 (m, 20H).

Step B 7-(2-Oxo-5-oxopyrrolidin-1-yl)-6-oxo-1-heptanoic Acid (14)

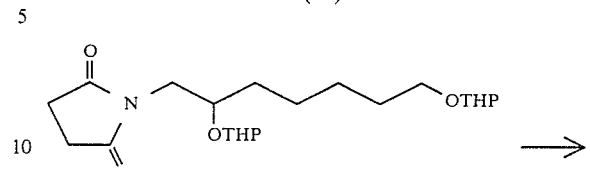

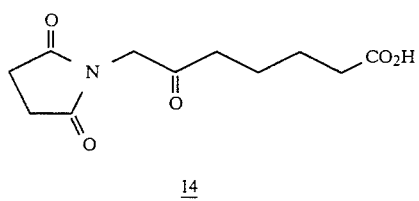

A mixture of 13 (132 mg, 0.33 mmol) and Jones reagent (1 mL) in acetone (5 mL) was stirred at 0° for one hour. It was then quenched with 2-propanol. After removal of the solvent and addition of saturated sodium chloride, the resulting aqueous solution was extracted three times with ether. The combined ether layer was washed with saturated sodium chloride and dried over magnesium sulfate. Removal of the solvent afforded 110 mg of crude 7-(2-oxo-5-oxopyrrolidin-1-yl)-6-oxo-1-heptanoic acid (14). IR ($CH_2Cl_2$): 3600–2400 (br), 1720 (br) cm$^{-1}$. A separate sample of the product, prepared by essentially the foregoing procedure was submitted for PMR (d$_6$-DMSO): δ 3.75–1.30 (m, 15H).

Step C 7-(2-Oxo-5-oxopyrrolidin-1-yl)-6,6-dimethoxy-1-heptanoic Acid, Methyl Ester (15)

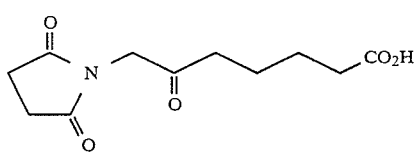

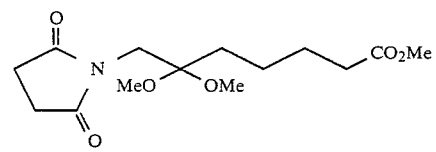

To a solution of crude 14 (110 mg) in methanol-methylene chloride (2 mL-1 mL) was added 0.5 mL of trimethyl orthoformate followed by 15 mg of PTSA. The mixture was stirred at room temperature for 1.5 hours. It was then diluted with ether and washed with saturated sodium chloride solution. The separated aqueous layer was extracted once with ether and the combined ether layer was dried over magnesium sulfate. Removal of the solvent gave 96 mg of crude methyl 7-(2-oxo-5-oxo-pyrrolidin-1-yl)-6,6-dimethoxy-1-heptanoate (15). A separate sample of the product, prepared by essentially the foregoing procedure, was submitted for analysis: IR (CH$_2$Cl$_2$): 1740 (br) cm$^{-1}$; PMR (CDCl$_3$): δ 3.65 (s, 9H), 2.75–1.25 (m, 14H); MS: m/z 270.1359 (M$^+$-OMe), calcd. for C$_{13}$H$_{20}$NO$_5$, 270.1342.

Step D

7-[2-(2-Hydroxy-2-methylheptylthio)-5-oxopyrrolidin-1-yl]6-oxoheptanoic Acid, Methyl Ester (16)

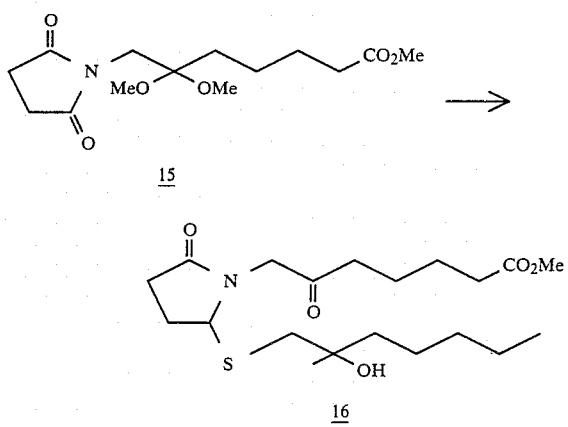

To a solution of 15 (50 mg, 0.16 mmol) in ethanol (2 mL) at 0° was added sodium borohydride (10 mg, 0.25 mmol). Two drops of 2N hydrochloric acid (in ethanol) were added at fifteen minute intervals for 1.5 hours. After continued stirring at 0° for one hour, the reaction was diluted with saturated aqueous sodium chloride and extracted three times with chloroform. The combined chloroform layer was dried over sodium sulfate. Removal of the solvent afforded 57 mg of the crude product which was dissolved in 2 mL of methylene chloride and treated with 20 mg of 1-mercapto-2-hydroxy-2-methylheptane in the presence of 15 mg of PTSA at room temperature overnight. It was then diluted with methylene chloride and washed with saturated sodium chloride solution. The separated aqueous layer was extracted twice with methylene chloride and the combined organic layer was dried over magnesium sulfate. The crude product was purified by preparative TLC to give 5.7 mg of methyl 7-[2-(2-hydroxy-2-methylheptylthio)-5-oxopyrrolidin-1-yl]-6-oxoheptanoate (16). IR (CH$_2$Cl$_2$): 1740, 1705 cm$^{-1}$; PMR (CDCl$_3$): δ 4.87 (t, 1H), 4.23 (AB, q, 2H), 3.67 (s, 3H), 2.70–1.20 (m, 22H), 1.20 (s, 3H), and 0.90 (t, 3H); MS: m/z 240.1227 (M$^+$-lower side chain), calcd. for C$_{12}$H$_{18}$NO$_4$, 240.1236.

EXAMPLE 4

7-[2-(2-Hydroxy-2-methylheptylthio)-5-oxopyrrolidin-1-yl]-6-hydroxyheptanoic Acid, Methyl Ester (17)

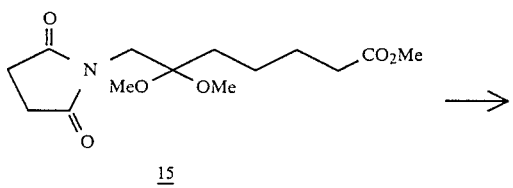

-continued

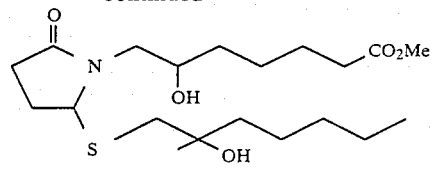

To a solution of 4 (96 mg, 0.3 mmol) in ethanol (3 mL) at 0° was added sodium borohydride (20 mg, 0.53 mmol). Three drops of 2N hydrochloric acid (in ethanol) were added at fifteen minute intervals for three hours. Concentrated hydrochloric acid was then added until pH=3. It was continually stirred at 0° for 45 minutes and then poured into saturated sodium bicarbonate solution. The separated aqueous layer was extracted with chloroform three times and the combined organic layer was dried over magnesium sulfate. The crude product was dissolved in 3 mL of methylene chloride and treated with 41 mg of 1-mercapto-2-hydroxy-2-methylheptane in the presence of 15 mg of PTSA at room temperature overnight. It was then diluted with ether, washed with water and dried over magnesium sulfate. The crude product was purified by preparative TLC to give 11 mg of methyl 7-[2-(2-hydroxy-2-methylheptylthio)-5-oxopyrrolidin-1-yl]-6-hydroxyheptanoate (17). IR (CH$_2$Cl$_2$): 3420, 1730, 1680 cm$^{-1}$; PMR (CDCl$_3$): δ 4.95 (t, 1H), 4.10–1.20 (m, 25H), 3.70 (s, 3H), 1.27 (s, 3H), 0.93 (t, 3H); MS: m/z 242.1385 (M$^+$-lower side chain), calcd. for C$_{12}$H$_{20}$NO$_4$, 242.1392.

EXAMPLE 5

7-[2-(2-Hydroxy-2-methylheptylthio)-5-oxopyrrolidin-1-yl]-6-hydroxyheptanoic Acid, Methyl Ester (17)

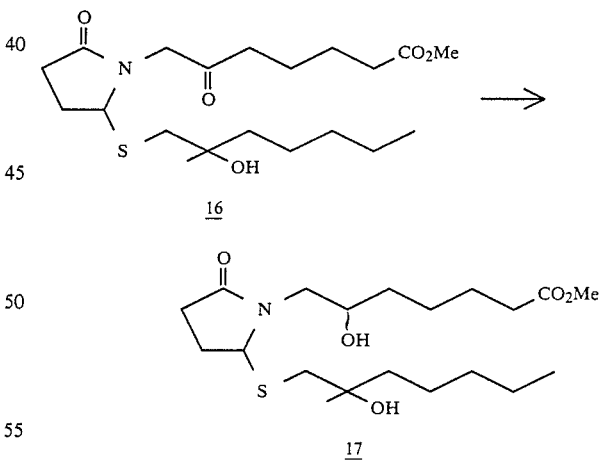

To a solution of 16 (about 4 mg) in ethanol (0.5 mL) at 0° was added sodium borohydride (3 mg). The mixture was stirred at 0° for one hour and then quenched with one drop of acetic acid. After removing ethanol, the residue was diluted with methylene chloride and washed with saturated sodium chloride. The separated aqueous layer was extracted with methylene chloride twice and the combined organic layer was dried over magnesium sulfate. Removal of the solvent gave 2.7 mg of methyl 7-[2-(2-hydroxy-2-methylheptylthio)-5-oxopyrrolidin-1-yl]-6-hydroxyheptanoate, 17. By comparison of TLC mobility, this product was determined to be identical in element content to that of Example 4.

The embodiments of the invention in which an exclusive property or privilege is claimed are defined as follows:

1. A compound of the formula:

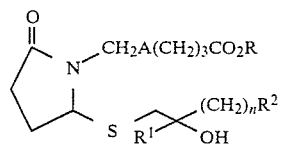

wherein
A is CH=CH (cis or trans), C≡C, CH₂CH₂,

or CHOHCH₂;
R is H, $C_1$ to $C_{12}$ n-alkyl, branched chain alkyl, or cycloalkyl, or a physiologically acceptable metal or amine salt cation;
$R^1$ is H, $CH_3$ or $C_2H_5$;
$R^2$ is $CH_3$ or $CF_3$; and
n is an integer from 4 to 9.

2. A compound according to claim 1 of the formula:

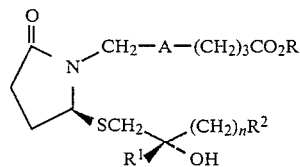

wherein R is H, $CH_3$ or $C_2H_5$, $R^1=R^2=CH_3$, and n is 4 to 6.

3. A compound according to claim 1 wherein A is $C_2H_4$, R is $C_2H_5$, n is 4, and $R^1$ and $R^2$ are each $CH_3$.

4. A compound according to claim 1 wherein A is $C_2H_4$, R is H, n is 4, and $R^1$ and $R^2$ are each $CH_3$.

5. A compound according to claim 1 wherein A is

R is $CH_3$, n is 4, and $R^1$ and $R^2$ are each $CH_3$.

6. A compound according to claim 1 wherein A is $CHOHCH_2$, R is $CH_3$, n is 4, and $R^1$ and $R^2$ are each $CH_3$.

7. A compound according to claim 2 wherein A is $C_2H_4$, R is $C_2H_5$, and n is 4.

8. A compound according to claim 2 wherein A is $C_2H_4$, R is H, and n is 4.

9. A compound according to claim 2 wherein A is $$\begin{matrix} CCH_2, \\ \| \\ O \end{matrix}$$

R is $CH_3$, and n is 4.

10. A compound according to claim 2 wherein A is $CHOHCH_2$, R is $CH_3$, n is 4, and $R^1$ and $R^2$ are each $CH_3$.

11. A physiologically acceptable metal salt of a compound according to claim 1.

12. A physiologically acceptable metal salt of a compound according to claim 2.

13. A physiologically acceptable amine salt of a compound according to claim 1.

14. A physiologically acceptable amine salt of a compound according to claim 2.

15. A pharmaceutical composition having cytoprotective activity comprising an effective amount of a compound according to claim 1 with a pharmaceutically acceptable carrier.

16. A method for preventing or treating ulcers in a human or an animal which comprises administering an effective amount of a pharmaceutical composition according to claim 15.

* * * * *